Figure 1:
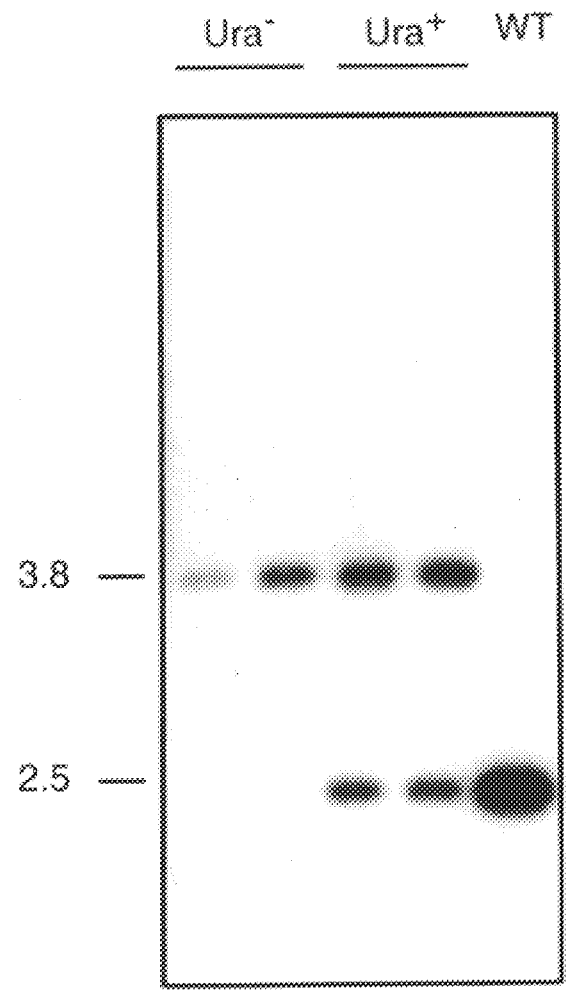

United States Patent [19]
Pelicic et al.

[11] Patent Number: 5,843,664
[45] Date of Patent: Dec. 1, 1998

[54] METHOD OF SELECTION OF ALLELIC EXHANGE MUTANTS

[75] Inventors: Vladimir Pelicic; Jean-Marc Reyrat; Brigitte Gicquel, all of Paris, France

[73] Assignee: Institut Pasteur, Paris, France

[21] Appl. No.: 661,658

[22] Filed: Jun. 11, 1996

[51] Int. Cl.$^6$ ............................ C12N 15/00; C12N 15/74; C12Q 1/68
[52] U.S. Cl. .......................... 435/6; 435/172.3; 435/320.1
[58] Field of Search ............................... 435/172.1, 172.3, 435/252.3, 253.1, 320.1, 6

[56] References Cited

PUBLICATIONS

Quandt, J. et al., "Versatile Suicide Vectors Which Allow Direct Selection For Gene Replacement in Gram–Negative Bacteria," *Gene*, pp. 15–21 (1993).

Stibitz, S., "Use of Conditionally Counterselectable Suicide Vectors For Allelic Exchange," *Meth. Enzymol*, vol. 235, pp. 458–465 (1994).

Kalpana, G.V. et al., "Insertional Mutagenesis and Illegitimate Recombination In Mycobacteria," Proc. Nat'l. Acad. Sci. USA, vol. 88, pp. 5433–5437 (Jun. 1991).

Cirillo, Jeffrey D. et al., "A Novel Transposon Trap for Mycobacteria:Isolation and Characterization of IS1096," *J. Bacteriol.*, vol. 173, No. 24, pp. 7772–7780 (Dec. 1991).

McAdam, R. et al., "In Vivo Growth Characteristics of Leucine and Methionine Auxotrophic Mutants of Mycobacterium bovis BCG Generated By Transposon Mutagenesis," *Infection and Immunity*, vol. 63, No. 3, pp. 1004–1012 (Mar. 1995).

Pelicic, V. et al., "Expression of the *Bacillus Subtilis* sacB Gene Confers Sucrose Sensitivity On Mycobacteria," *J. Bacteriol.*, vol. 178, No. 4, pp. 1197–1199 (Feb. 1996).

Sander, P. et al., "rpsL: A Dominant Selectable Marker For Gene Replacement In Mycobacteria," *Mol. Microbiol.*, vol. 16, No. 5, pp. 991–1000 (1995).

Reyrat, J.M. et al., "The Urease Locus of *Mycobacterium Tuberculosis* and Its Utilization for the Demonstration of Allelic Exchange in *Mycobacterium Bovis* Bacillus Calmette–Guerin,"*Proc. Nat'l. Acad. Sci. USA*, vol. 92, pp. 8768–8772 (Sep. 1995).

Norman, E. et al., "Gene Replacement By Homologous Recombination In *Mycobacterium Bovis* BCG," *Mol. Microbiol.*, vol. 16, No. 4, pp. 755–760 (1995).

Marklund, B.I. et al., "Gene Replacement Through Homologous Recombination In Mycobacterium Intracellular," *J. Bacteriol.*, vol. 177, No. 21, pp. 6100–6105 (Nov. 1995).

Husson, R. et al., "Gene Replacement and Expression of Foreign DNA in Mycobacteria," *J. Bacteriol.*, vol. 172, No. 2, pp. 519–524 (Feb. 1990).

Balasubramanian, V. et al., "Allelic Exchange in *Mycobacterium Tuberculosis* With Long Linear Recombination Substrates," *J. Bacteriol.*, vol. 1978, No. 1, pp. 273–279 (Jan. 1996).

Aldovini, A. et al., "The uraA Locus and Homologous Recombination In *Mycobacterium Bovis* BCG," *J. Bacteriol.*, vol. 175, No. 22, pp. 7282–7289 (Nov. 1993).

*Primary Examiner*—George C. Elliott
*Assistant Examiner*—Robert Schwartzman
*Attorney, Agent, or Firm*—Finnegan, Henderson, Farabow, Garrett & Dunner, L.L.P.

[57] ABSTRACT

A process for replacing a nucleotide sequence in the genome of a mycobacterium strain comprises the steps of:

a) providing a vector containing SacB gene coding for levane saccharase enzyme and a nucleotide sequence of interest;

b) transfecting the mycobacterium strain with the vector;

c) selecting clones of the resulting transfected mycobacteria for replacement of the nucleotide sequence of interest by propagating the transfected clones in a culture medium supplemented with sucrose; and d) isolating the recombinant strain.

The process is useful for positive selection of allelic exchange mutants, such as in *Mycobacterium tuberculosis* complex.

26 Claims, 12 Drawing Sheets

METHOD OF SELECTION OF ALLELIC EXHANGE MUTANTS

BACKGROUND OF THE INVENTION

Recently developed techniques for introducing and expressing genes in mycobacteria have opened the way for molecular genetic manipulation as a means to obtain further understanding of these species (Jacobs et al., 1991). Usually, virulence factors are genetically characterized following Koch's molecular postulates (Falkow, 1988): (i) cloning of the gene of interest; (ii) effects on the virulence of specific inactivation of the gene; and (iii) restoration of the pathogenicity by complementing with the wild-type allele. However, the genetic analysis of mycobacteria has been hampered by a lack of efficient tools for generating defined mutants by homologous recombination (Jacobs, 1992).

The 'reverse genetics' approach to understanding gene function is to specifically disrupt the gene of interest by exploiting the homologous recombination properties of the cell to replace the functional allele with an inactivated copy (Ruvkun and Ausubel, 1981). Usually, the gene is inactivated by the insertion of an antibiotic-resistance marker, such that the recombination event is easily detected on a selective medium. It was demonstrated that this methodology is applicable to *Mycobacterium smegmatis* using the pyrF gene (Husson et al., 1990). However, performing allelic exchange has been relatively cumbersome due to the rarity of double-cross-over events, requiring an extensive screening to isolate a gene-exchange mutant. This method has proven particularly inefficient in slow-growing mycobacteria where homologous recombination is less frequent than illegitimate recombination, i.e. recombination at a site other than the selected gene by an unknown mechanism. Several workers have been unable to detect any gene replacement (Aldovini et al., 1993; Kalpana et al., 1991). However, several recent studies have succeeded in identifying allelic exchange, albeit at low frequency, in slow-growing mycobacteria (Marklund et al., 1995; Norman et al., 1995; Reyrat et al., 1995; Balasubramanian et al., 1996). Clearly, allelic exchange would greatly benefit from a system allowing positive selection of mutants resulting from gene replacement.

High levels of illegitimate recombination and low frequency of recombination have also been described in gene-replacement experiments in eukaryotic cells and some bacteria (Cai and Wolk, 1990; Desomer et al., 1991). These problems can be overcome by employing a double-selection strategy (Stibitz, 1994). The vector used for mutagenesis should bear an antibiotic marker for the primary selection of transformants, and a second marker with a conditionally dominant lethal effect to counter-select clones which have lost the vector DNA, eliminating the need for extensive screening. No counter-selectable marker was available for mycobacteria until recently, when the rpsL gene was shown to exhibit a dominant lethal effect in *M. smegmatis*. It was used to demonstrate that double selection is possible in this bacterium (Sander et al., 1995).

There has existed a need to design a general method for gene exchange mutagenesis, which would overcome the problems arising from high levels of illegitimate recombination and low frequency of homologous recombination. A possible strategy, based on the use of much longer stretches of linear homologous DNA (20 kb or more) was recently proposed (2). In this way, it was shown that the frequency of homologous recombination for the *M. tuberculosis* leuD gene could be increased. The proportion of allelic exchange mutants rose from an undetectable level to approximately 6% of the transformants (2). However, a possible limitation to this methodology is the fact that manipulation of cosmids is relatively difficult due to their extensive length.

SUMMARY OF THE INVENTION

In our rationale, the easier way to deal with those difficulties would be to use a conditionally dominant lethal marker in a double-selection strategy (20). This marker, present on the suicide delivery vector, would be inserted into the chromosome of the clones resulting from single homologous recombination or illegitimate recombination events, leading to their death on selective medium. The resulting effect would be an increase of the proportion of allelic exchange mutants, making the screening of transformants easier. Recently, two counter-selectable markers have been described in *M. smegmatis* and used to demonstrate that positive selection of allelic exchange mutants was possible in this bacterium: (i) the rpsL gene conferring a dominant phenotype of sensitivity to streptomycin (18), and (ii) the *Bacillus subtilis* SacB gene conferring sensitivity on sucrose (13, 14).

SacB revealed itself a powerful tool because it can be used for the positive selection of mutants in either single-step or two-step selection strategies (14). In a single-step protocol, a suicide vector was electroporated into *M. smegmatis* and the allelic exchange mutants were directly selected on sucrose. In a two-step selection, we first selected a single recombination transformant and propagated it in liquid broth to allow a second crossing-over to happen. Then by plating on sucrose, the mutants that have lost the SacB gene during the second crossing-over could be positively selected (14). It was not apparent that this latter possibility should be of particular interest in slow-growing mycobacteria. Indeed, a one-step selection would be unadapted for numerous genes where double recombinants are undetectable in a classical experiment (7, 17).

Even if SacB was shown to confer sucrose sensitivity on slow-growing mycobacteria (13), the demonstration of its use as a marker for positive selection of allelic exchange mutants had yet to be done. A two-step selection protocol was explored in slow-growing mycobacteria with the ureC gene as a model.

Accordingly, this invention provides a process for replacing a nucleotide sequence in the genome of a mycobacterium strain. The process comprises providing a vector containing a SacB gene coding for levane saccharase enzyme and a nucleotide sequence of interest. The mycobacterium strain is transfected with the vector. Clones of the resulting transfected mycobacteria are selected for replacement of the nucleotide sequence of interest by propagating the transfected clones in a culture medium supplemented with sucrose. The recombinant strain can be isolated, if desired. Typical mycobacterium strains are *M. tuberculosis, M. smegmatis,* and *M. bovis.* In a preferred embodiment of this invention, the mycobacterium is a slow growing mycobacterium.

In a preferred embodiment of this invention, the vector employed in the process contains a marker gene, and the selection step is preceded by a first selection step of the clones by propagating the clones in a culture medium supplemented with a selection molecule. For example, the marker gene can be a gene coding for resistance to an antibiotic, such as gentamycin.

The nucleotide sequence of interest can be an endogenous gene of the mycobacteria to be transfected. The nucleotide sequence can be modified by addition, substitution, or deletion of at least one nucleotide. Alternatively, the nucleotide sequence of interest can be exogenous with respect to the mycobacteria to be transfected. In another embodiment of the invention, the nucleotide sequence to be replaced can be a plasmid or a chromosomal nucleotide sequence.

In still another embodiment, the nucleotide sequence of interest can be a hybrid molecule coding for a fusion polypeptide. This invention also provides a process of the type described, wherein the fusion polypeptide contains an antigenic determinant heterologous with respect to the mycobacterium strain to be transfected, the antigenic determinant being much more recognized by the sera of patients than the initial endogenous antigenic determinant.

This invention also provides recombinant mycobacterium strains. The strains can have a modified nucleotide sequence in their genomes, differ from wild-type sequences of said mycobacterium, and the recombinant mycobacterium strains may or may not contain sequences from an insertion vector.

This invention further provides recombinant vectors, which are particularly suitable for use in the invention.

Finally, this invention provides a method of selecting mycobacteria sensitive to sucrose. The method comprises cultivating mycobacteria in a culture medium supplemented with sucrose; cultivating in parallel the same mycobacteria in a culture medium without sucrose; and selecting clones sensitive to sucrose having a genome that contains SacB gene.

BRIEF DESCRIPTION OF THE DRAWINGS

This invention will be more fully understood with reference to the drawings in which:

FIG. 1 is a Southern-blot analysis of representative clones resulting from homologous recombination obtained either by a one-step selection or by a two-step selection on sucrose. Two Ura$^-$ and two Ura$^-$ clones are presented. WT indicates *M. smegmatis* wild-type DNA. Genomic DNA was digested with Sphl and hybridized with a 2.5 kbp Sphl fragment carrying the pyrF gene.

FIG. 2 shows a general strategy for generating unmarked mutations in mycobacteria using a two-step selection methodology. The first selection is performed on plates with gentamicin (LUG). The second selection step is performed on LUS to select positively for the clones that have lost the SacB gene, pyrF* and SacB* indicate mutant alleles of those genes.

FIG. 3 is a Southern-blot analysis of various clones resulting from the integration of pPR34 during a two-step selection strategy as described in FIG. 2. Genomic DNA was digested with Sphl and hybridized with the pyrF probe.

FIG. 4 is a Southern-blot analysis of representative clones, 5 Ure$^-$ and 6 Ure$^+$, obtained after the selection on 2% sucrose (SECOND STEP). Two controls have been included, BCG is for *M. bovis* BCG wild-type DNA and BCG::pPR24 is a single recombinant. Genomic DNA was digested with PstI and hybridized with the pPR24 vector as a probe.

FIG. 5 shows a General strategy for allelic exchange mutagenesis using a two-step selection on 2% sucrose. In the first step, a single recombinant is selected on kanamycin or gentamycin. In the second step, clones that have lost the SacB gene are positively selected on 2% sucrose. SacB* indicate a mutant allele of the SacB gene. Abbreviations: ureA, ureB, and ureC are the three subunits of the mycobacterial urease (16); Km, Tn903 gene encoding kanamycin resistance; Gm, aacCI gene encoding gentamicin resistance; ori, *E. coli* origin of replication.

FIG. 6 is a map describing plasmid pPR26.

FIG. 7 is a map describing plasmid pPR34.

FIG. 8 is a map describing plasmid pPV23(1).

FIG. 9 is a map describing plasmid pPR27.

FIG. 10 is a map describing plasmid pPR25.

FIG. 11 is a map describing plasmid pPR24.

FIG. 12 is a map describing plasmid pPR2.

DESCRIPTION OF PREFERRED EMBODIMENT

It has been demonstrated that the *Bacillus subtilis* SacB gene, encoding the secreted enzyme levansucrase (sucrose: 2,6-β-o-fructan 6-β-o-fructosyltransferase; EC 2.4.1.10), confers sucrose sensitivity to mycobacteria on 10% sucrose (Pelicic et al., 1996). The efficiency of selection, $5\times10^{-4}$ for *M. smegmatis* and $10^{-6}$ for *Mycobacterium bovis* BCG, is comparable to that for other bacteria where SacB has been used for positive selection of allelic exchange (Cai and Wolk, 1990; Cianciotto et al., 1988; Kaniga et al., 1991; Kamoun et al., 1992; Schäfer et al., 1994; Schweizer, 1992). The possibility of using SacB as a positive-selection system for gene-replacement events in mycobacteria was tested. The pyrF gene of *M. smegmatis* was chosen as a model because it has previously been used in homologous recombination experiments in this species. pyrF mutants are uracil auxotrophs and can thus be easily screened. It was found that pyrF mutants resulting from allelic-exchange events were readily identified by either a one-step or a two-step selection on sucrose. Using a two-step selection, uracil auxotrophic mutants were isolated with an unmarked, defined mutation in the pyrF gene. These results illustrate how SacB can be used to facilitate experiments involving allelic-exchange events in mycobacteria.

One-step Selection of pyrF Allelic Exchange pJQ200 is a cloning vector carrying a gentamycin-resistance gene active mycobacteria, and the SacB gene of *B. subtilis* (Quandt and Hynes, 1993). The pyrF gene disrupted by the aph cassette, conferring resistance to kanamycin, (pyrF::Km), was obtained from pY6002 (Husson et al., 1990) and inserted in pJQ200 to give pPR26. pPR26 was used to transform *M. smegmatis* by electroporation. The transformants resulting from homologous integration were selected on Luria-Bertani (L) medium supplemented with uracil (LU), and containing either (i) kanamycin (LUK) as a classical test for the frequency of recombination or (ii) kanamycin and sucrose (LUKS) to assess the possibility of sucrose selection. The electroporation of 1 μg of vector resulted in approx. 100 transformants on LUK and only approx. 5 on LUKS plates, a 20-fold decrease. In the same conditions, pY6002, which lacks the SacB gene, gave the same number of colonies on LUK and LUKS plates (data not shown). Thus SacB, present on pPR26, is responsible for the death of the majority of the transformants when selection is performed on sucrose.

The phenotypes of the transformants were characterized by replica plating on different selective media. Most of the clones (95%) selected on LUK plates were kanamycin resistant ($Km^R$), gentamicin resistant ($Gm^R$), sucrose sensitive ($Suc^S$), uracil positive (Ura$^-$) and resulted from single recombination events in the pyrF gene (Table 1).

TABLE 1

Effects of the presence of sucrose on the proportion of pyrF allelic-exchange mutants recovered from a one-step selection after transformation with pPR26.

| | Percent of total clones (%)[a] | |
|---|---|---|
| Growth medium | Ura⁻, Km$^R$, Gm$^S$ (allelic exchange) | Ura⁻, Km$^R$, Gm$^R$ (simple recombination) |
| LUK | 5 | 95 |
| LUKS | 100 | 0 |

[a]Mean value of two independent experiments.

Genomic DNA from these transformants was analyzed by Southern blotting with a pyrF probe. These clones contained a complete copy of pPR26 inserted into the pyrF gene, thus possessing both an intact (2.5 kbp) and an inactivated copy of pyrF (3.8 kbp) (FIG. 1). The remaining clones 5% were true uracil auxotrophs, with the phenotype Km$^R$, Gm$^S$, Suc$^R$, Ura⁻. The endogenous allele of the pyrF gene, corresponding to a SphI fragment of 2.5 kbp on a Southern blot, had been replaced by the inactivated copy corresponding to a fragment of 3.8 kbp (FIG. 1). The increase of 1.3 kbp corresponds to the size of the kanamycin-resistance gene which was used to inactivate pyrF. Moreover, no hybridization signal was detected in the auxotrophs when the vector pJQ200 was used as a probe (data not shown), indicating that the vector sequence had been lost.

All the transformants (100%) selected on the LUKS plates exhibited the Km$^R$, Gm$^S$, Suc$^R$, Ura⁻ phenotype and were uracil auxotrophs generated by allelic exchange at the pyrF gene (Table 1). This was confirmed by Southern-blot analysis, which gave hybridization patterns indistinguishable from those observed for the auxotrophs obtained on LUK plates. See (FIG. 1). One-step selection on sucrose was 100% efficient, because all of the clones corresponding to single recombination events (incorporation of the entire vector bearing the SacB gene) was eliminated. Thus, when a suicide vector bearing the SacB gene is used for the homologous recombination experiments, mutants resulting from an allelic exchange can be directly selected by plating on sucrose.

Two-step Selection Method

The possibility of selecting allelic-exchange events in two steps was next investigated. This procedure might be useful if the frequency of gene exchange for a gene of interest is too low to recover mutants in one step. For the first step, an individual clone was chosen at random from those obtained on a LUK plate in the previous experiment. It was verified that this clone corresponded to a single recombination event in the pyrF gene by phenotypic (Km$^R$, Gm$^R$, Suc$^S$, Ura⁺) and Southern-blot analysis. The clone was propagated overnight in 7H9 medium (Difco) supplemented with uracil (without antibiotic selection) to allow a deletion-recombination event to occur at the pyrF locus. Any such event could either eliminate the wild-type or the interrupted allele of the pyrF gene. The culture was spread on LUKS plates (step 2) to select cells which had lost the SacB gene. Several thousands of colonies were obtained and approx. 200 clones were analyzed. Two-thirds were uracil auxotrophs as verified by phenotypic analysis (Table 2) and Southern hybridization (FIG. 1). The remaining colonies (⅓), through Suc$^R$, were not uracil auxotrophs (Km$^R$, Gm$^R$, Suc$^R$, Ura⁺) and presumably corresponded to clones with a mutation in the SacB gene.

TABLE 2

Effects of the presence of sucrose on the proportion of pyrF allelic-exchange mutants recovered from a two-step selection.

| | | Percent of total clones (%)[b] | | |
|---|---|---|---|---|
| Transforming DNA | Growth medium[a] | Ura⁻, Gm$^S$ Suc$^R$ (allelic exchange) | Ura⁺, Gm$^R$ Suc$^R$ (SacB mutants) | Ura⁺ (revertants) |
| pPR28 | LUKS | 66 | 34 | ND |
| pPR26 | LUS | 35 | 7 | 58 |
| pPR34 | LUS | 27 | 4 | 69 |

[a]Medium used in the second step of selection.
[b]At least 192 clones were analyzed in each experiment.
ND, not detectable Genomic DNA was probed with pJQ200 by Southern blotting: this showed that the SacB mutations were either point mutations (no change of vector size) or 2 kbp insertions possibly resulting from the insertion of a transposable element (data not shown). It is possible that the trapped sequence corresponds to IS 1096, which was discovered in *M. smegmatis* using a similar methodology with β-galactosidase as a reporter gene (Cirillo et al., 1991). This suggests that SacB can be used as a transposon trap in *M. smegmatis*, as it has been used in *Escherichia coli* (Gay et al., 1985).

The experiment was repeated, but with the second selection step on sucrose plates without kanamycin (LUS). Three times more colonies were obtained at the same dilution than by selection on LUKS plates. Thus, the majority of the clones on LUS plates were expected to be sensitive to kanamycin and to have resulted from loss of the interrupted allele of pyrF (pyrF::Km), and thus the Km cassette. This was verified by phenotypic (Km$^S$, Gm$^S$, Suc$^R$, Ura⁺) (Table 2) and Southern-blot analysis (FIG. 1). A small proportion of the clones (7%) resulted from mutations in the SacB gene. But a significant proportion of the clones obtained were uraxil auxotrophs (1 in 3), and corresponded to allelic-exchange mutants. Therefore, positive selection of allelic-exchange events is possible on sucrose using a two-step methodology, even when no antibiotic selection was applied during the second step of selection.

Generation of Unmarked Mutants

Figure 2:
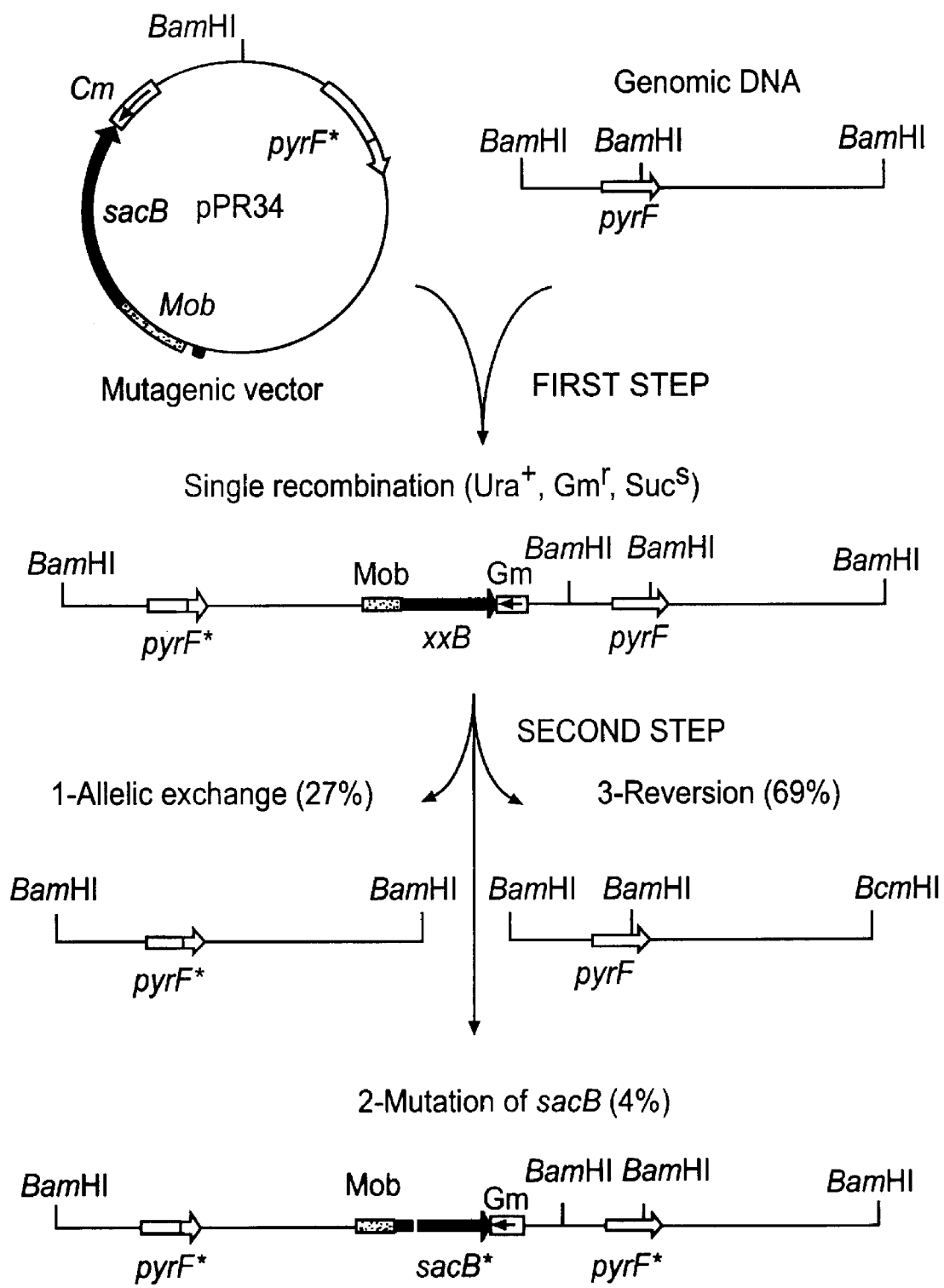

The feasibility of a two-step selection, in the absence of antibiotic selection during the second step, suggested that it might be possible to generate unmarked mutants as described for other bacteria (Donnenberg et al., 1991; Ried and Colimer, 1987; Schafer et al., 1994; Soupène et al., 1995). The aph gene was excised with BamHI from the mutated allele pyrF::Km (Husson et al., 1990) and a frameshift mutation was generated by blunting the ends with T4 DNA polymerase and religating. This unmarked mutated copy of the pyrF gene (pyrF*) was inserted into pJQ200 to generate pPR34 (FIG. 2).

pPR34 was used to transform *M. smegmatis* by electroporation, and clones resulting from a single homologous recombination event were selected on LU supplemented with gentamicin (LUG): the PJQ200 vector carries the sacCl gene conferring gentamicin resistance (Quandt and Hynes, 1993). The phenotype and Southern-blot analyzes confirmed that the selected clones resulted from a single cross-over in the pyrF gene (data not shown). As described above, the second step of selection was performed on LUS medium. The clones were replica plated onto M63 minimal medium. Approximately ⅓ of the clones were unable to grow on minimal medium and were thus uracil auxotrophs (Table 2). This is consistent with the results of the previous experiment with pPR26, with no selective pressure for the antibiotic resistance during the second step (Table 2).

Figure 3:
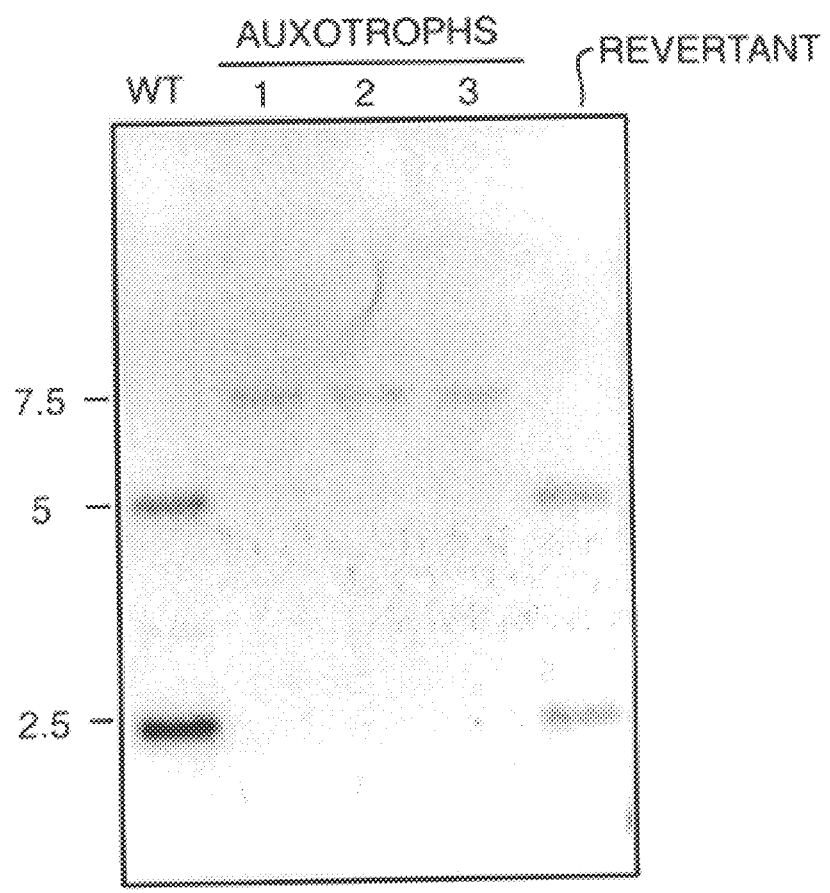

As the frameshift mutation introduced into the pyrF gene destroyed a BamHl site, allelic-exchange mutants identified by their auxotrophic phenotype should have a different hybridization pattern in a Southern-blot analysis with BamHl-cut DNA. Several Ura$^+$ revertants and Ura$^-$ mutants were analyzed by Southern blotting. As expected, the revertant clones presented two fragments of 2.5 kbp and 5 kbp hybridizing to the pyrF probe. The unmarked auxotrophic mutants gave a single hybridizing BamHl fragment of 7.5 kbp, confirming the loss of the central BamHl site (FIG. 3). Thus, a two-step selection with sucrose selection in the second step enabled us to isolate unmarked mutants carrying a known, specific lesion in the pyrF gene.

In summary, a double-selection strategy was recently adapted to M. smegmatis using the rpsL gene as a counter-selectable marker (Sander et al., 1995). However, its applicability to slow-growing mycobacteria has not been described. rspL is a dominant marker conferring susceptibility to streptomycin to a streptomycin-resistant strain which carries a mutation in the endogenous rpsL allele. When used as a counter-selectable marker, rpsL leads to allelic-exchange mutants resistant to streptomycin, an antibiotic, which is still a common component of several combined antituberculosis chemotherapeutic regimens (WHO, 1991).

SacB presents several interesting characteristics making it a useful counter-selectable marker for the positive selection of gene-exchange events in mycobacteria. First, SacB does not require an antibiotic-resistant strain to induce lethality. Second, SacB can be used in two-step selection strategies. This approach will prove useful in cases where the frequency of allelic exchange for the gene of interest is too low for one-step selection. Third, the efficiency of selection on sucrose in a two-step strategy is sufficiently high to detect rare deletions that give rise to unmarked defined mutants. Although antibiotic markers are useful for genetic studies, an unmarked mutant is necessary when generating strains for use as new vaccines. Moreover, in the construction of strains with multiple mutations there is no need for a corresponding number of antibiotic-resistance markers.

The expression of SacB, the *Bacilus subtilis* gene encoding levansucrase, is lethal to mycobacteria in the presence of 10% sucrose. The use of SacB as a marker for positive selection of gene-replacement events into *Mycobacterium smegmatis* is herein described. A sucrose counter-selectable suicide plasmid was used to deliver an inactivated copy of the pyrF gene (pyrF::Km) into the *M. smegmatis* genome. Only uracil auxotroph clones, resulting from replacement of the endogenous pyrF allele, survived in a one-step selection on plates containing kanamycin and 10% sucrose. This demonstrated that selection on sucrose against the maintenance of the vector bearing the SacB gene is 100% efficient, enabling the positive selection of allelic-exchange mutants. Two-step selection is also feasible; it was used to construct unmarked pyrF mutants in which the gene was inactivated by a frameshift mutation. This method of generating unmarked, directed mutations is rapid and simple, making it a powerful tool for the genetic characterization of mycobacteria.

This invention will be described in more detail in the following Examples.

Experimental Procedures

Bacterial Strains and Media

The bacterial strains and plasmids used in this study are listed in Table 3. *E. coli* was routinely grown on liquid or solid Luria-Bertanl (L) medium, and kanamycin and gentamicin were used at 20 $\mu$g ml$^{-1}$. *M. smegmatis* was grown on liquid Middlebrook 7H9 medium (Difco) supplemented with 0.2% glycerol and 0.05% Tween, or on solid L medium. When required, antibiotics were included at the following concentrations: kanamycin, 20 $\mu$g ml$^{-1}$; and gentamicin, 5 $\mu$g ml$^{-1}$.

TABLE 3

Bacterial plasmids and strains used in this study.

| Strain/Plasmid | Relevant characteristics | Source/Reference |
|---|---|---|
| Strain | | |
| *E. coli* Dh5α | φ80dlacZΔM15 recA1 endA1 hsdR17 (r$^-$, m$_k$$^-$) | Gibco BRL |
| *M. smegmatis* mc 155 | Highly transformable mutant | Snapper et al. (1990) |
| Plasmid | | |
| pY6001 | pUC19 with the pyrF gene of *M. smegmatis* on a Sau3A1 fragment | Husson et al. (1990) |
| pY6002 | Insertion of the aph cassette in BamHl of pY6001 resulting in pyrF::Km | Husson et al. (1990) |
| PJQ200 | Cloning vector with SacB and aacC1 | Quandt and Hynes (1993) |
| pPR2b | pjQ200 with pyrF::Km on an Xbal-Mlul fragment of pY6002 | This work |
| pPR33 | Excision of the aph gene from pY6002 and blunting resulting in pyrF$^+$ | This work |
| pPR34 | PJQ200 with pyrF$^+$ on an xbal-Mlul fragment of pPR33 | This work |

Transformants were selected on LU medium (L medium with 0.2 mM uracil) supplemented with kanamycin (LUK) or gentamicin (LUG). 10% sucrose was added where indicated (LUS or LUKS plates). Uracil auxotrophs were identified by their inability to grow on M63 minimal medium with glucose as the sole carbon source.

DNA Manipulations

Restriction enzymes, T4 DNA polymerase, and T4 DNA ligase were purchased from Boehringer Mannheim, Amersham, and Gibco BRL, respectively. All enzymes were used in accordance with the manufacturer's recommendations. Plasmid DNA was isolated by Qiagen preparation (Qiagen Inc.). DNA fragments used in the cloning procedures and for radiolabelling were gel purified using the Geneclean II kit (BIO 101 Inc.).

Electrotransformation of Bacteria

Electrocompetent bacteria were prepared by the method of Sander et al. (1995) with minor modifications. Bacteria were grown in 400 ml of L (*E. coli*) or 7H9 medium (*M. smegmatis*) to an OD$_{600}$ of )0.4. After three washings in 10% glycerol, the cells were resuspended in 1 ml 10% glycerol. Aliquots (100 $\mu$l) of freshly prepared mc$^2$155 cells were electroporated with 1 $\mu$g of vector DNA in 0.2 cm cuvettes (Bio-Rad) with a single pulse (2.5 kV, 25 $\mu$F, 200 ohms). After 3–4 days of incubation, single colonies were picked and resuspended in 7H9 medium aliquoted in 96-well microtiter plates. Forty-eight clones were replicated simultaneously on different selective media using a replica plater (Sigma).

Isolation of Genomic DNA, and Southern Analysis

Mycobacterial genomic DNA was isolated as follows: cells from a 5 ml culture were pelleted by centrifugation (15 min, 5000×g). The pellet was resuspended in 250 µl of solution 1 (25% sucrose, 50 mM Tris-HCl pH 8.0, 50 mM EDTA, 500 µg ml$^{-1}$ lysozyme) and incubated overnight at 37° C. Two hundred and fifty microliters of solution II (100 mM Tris-HCl pH 8.0, 1% SDS, 400 µg ml$^{-1}$ proteinase K) was then added and the samples incubated for 4h at 55° C. DNA was then extracted twice with phenol-chloroform, and concentrated by ethanol precipitation.

One microgram of genomic DNA was digested overnight with an excess of restriction enzyme (30 U) and separated by electrophoresis using 0.7% agarose gels. Southern blotting was performed in 20×SSPE (150 mM NaCl, 8.8 mM NaH$_2$PO$_4$, 1 mM EDTA, pH 7.4) using Hybond-N+nylon membranes (Amersham) with standard methods (Sambrook et al., 1989). The Megaprime random-primed labelling kit (Amersham) and 5 µmCl of [α-$^{32}$P]-dCTP were used to label probes. Non-incorporated label was removed by filtration through a Nick Column (Pharmacia). Prehybridization and hybridization were performed at 65° C. using RH buffer (Amersham), as recommended by the manufacturer, Serial 15 min washings were performed at 65° C. as follows: two washes with (2×SSPE, 0.1% SDS), one wash with (1×SSPE, 0.1% SDS) and two washes with (0.7×SSPE, 0.1% SDS). Blots were exposed overnight to X-Omat AR X-ray film (Kodak) at −80° C.

Construction of Vectors pPR26 was constructed by inserting the blunt-ended Xbal-Mlul fragment (5.9 kbp), containing the pyrF::Km allele excised from pY6002 (Husson et al., 1990), into the Smalcut pJO200 vector (Quandt and Hynes, 1993). The aph cassette used to inactivate the pyrF gene was excised from pY6002 by BamHl digestion, and a frameshift mutation was introduced in the pyrF gene (pyrF$^+$) by blunting with the T4 DNA polymerese and religation, resulting in pPR33. pPR34 was constructed by cloning a blunt-ended Xbal-Mlul fragment (4.6 kbp), containing the mutated copy pyrF$^+$, into the Smal site in pJO200.

pY6001 (Husson et al., 1990) was reconstructed during pPR33 construction, by omitting the blunting step before the religation. The 2.5 kbp Sphl fragment of pY6O01 corresponding to the pyrF gene was used as a probe in the Southern-blot experiments.

Over the last decade, the genetic characterization of mycobacteria has greatly benefited from the development of efficient genetic systems, resulting in the identification of several genes that could play a role in virulence (5). However, the construction of defined mutants leading to a better understanding of the physiopathology of tuberculosis is still hampered by the great difficulty to perform allelic exchange (6).

Due to the rarity of double-crossover events and the high levels of illegitimate recombination, the isolation of a gene exchange mutant is always cumbersome, if possible at all. Despite those difficulties, allelic exchange in the fast-growing M. smegmatis has early been achieved (4) using a traditional protocol of mutagenesis (17); a gene inactivated in vitro by the insertion of an antibiotic resistance marker is delivered on a suicide vector into the bacteria. Anyhow, the proportion of allelic exchange mutants was variable and generally low, representing less than 10% of the transformants (4, 14, 18). The ratio, double-crossover towards single recombination and illegitimate recombination, is even more unfavorable in slow-growing mycobacteria. This partly explains why the first attempts to perform allelic exchange in mycobacteria from the M. tuberculosis complex were unsuccessful (1, 8).

Nevertheless, it has been demonstrated that allelic exchange was possible in M. bovis BCG using the ureC gene coding for a subunit of the urease (16). Reyrat et al. took advantage of the fact that urease activity can be monitored with a simple calorimetric test, which facilitated the otherwise time consuming screening step of transformants (16). Ure clones represented only 4% of the transformants. Simultaneously, two other groups succeeded in identifying low-frequency allelic exchange in slow-growing mycobacteria (10, 12).

The overall proportion of double recombinants is thus generally lower than M. smegmatis and it depends essentially on the selected gene. Moreover, the frequency of homologous recombination for several different genes leuD (2), purC (7), is too low to enable the detection of double recombinants in a classical gene exchange experiment (17).

Expression of SacB is lethal to mycobacteria in the presence of sucrose SacB, making it a useful counter-selectable marker for positive selection of gene replacement events as demonstrated in the fast-growing Mycobacterium smegmatis. Following the same methodology, a sucrose counter-selectable vector was used to deliver, into the Mycobacterium bovis BCG genome, an inactivated copy (ureC::Km) of the ureC gene encoding the mycobacterial urease. A two-step selection procedure on 2% sucrose allowed the positive selection of gene exchange mutants. This technique should thus be an extremely useful facility for the genetic analysis of pathogenic mycobacteria.

Selection of a ureC Single-recombinant

As for the experiments in M. smegmatis, the sucrose counter-selectable suicide vector we used was pJQ200 (15). The ureC::Km mutated allele was excised from pJΔ64K (16) on a SacI-KpnI fragment, which was made blunt-ended and inserted into SmaI-cut pJQ200 to give rise, following the orientation of the insert, to pPR24 or pPR25. pPR24 was selected at random for the subsequent experiments and used to transform M. bovis BCG by electroporation. However, the results are similar when using pPR25 (data not shown).

The transformants, resulting either from homologous or illegitimate recombination of pPR24 into the chromosome, were selected on 7H10 medium supplemented with kanamycin. The electroporation of one µg of closed circular (cc) pPR24 vector resulted in approximately 200 transformants, thus the frequency of transformation was similar to that when pJΔ64K was used (16). Transformant colonies were phenotypically characterized using the urea/indol colorimetric test (11): a red coloration was scored as Ure$^+$, whereas a yellow coloration is considered as Ure$^-$. Only 4% of the transformants were Ure$^-$ and resulted thus from an allelic exchange event (Table 4).

TABLE 4

Effects of the presence of 2% sucrose on the proportion of ureC allelic exchange mutants.

| Medium[a] | Percent of total clones (%)[b] | |
|---|---|---|
| | Ure[−c] | Ure[+c] |
| without sucrose (one step) | 4 | 96 |
| with 2% sucrose (two-step) | 26 | 74 |

[a]The selective medium was 7H10 supplemented with kanamycin (20 μg · ml$^{-1}$).
[b]50 clones were analyzed.
[c]Ure$^-$: no change of color; Ure$^+$: change of the color to red.

The results were absolutely in accord with what was already described by Reyrat et al. in the initial allelic exchange experiments (16).

Figure 4:
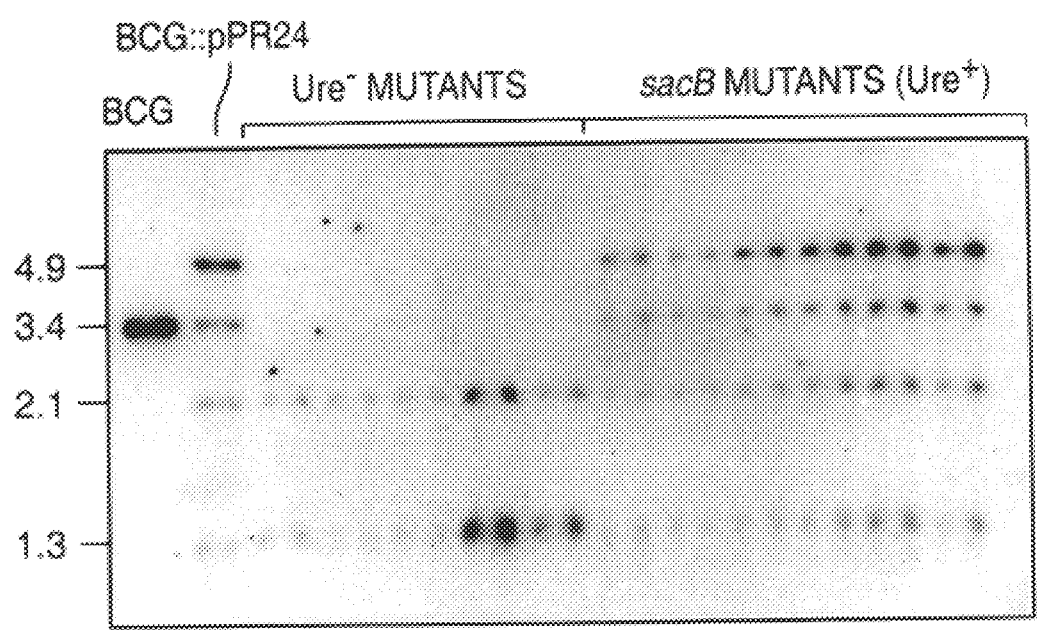

For a two-step selection on sucrose as already described for *M. smegmatis* (14), one need to select a clone corresponding to a single-recombination event in the target gene. Five randomly chose Ure$^+$ transformants were propagated in 7H9 until saturation. The genomic DNA was extracted and analyzed by Southern-blotting using the vector pPR24 as a probe. Surprisingly, all the clones corresponded to single homologous recombination events and contained a complete copy of pPR24 inserted into the ureC gene (FIG. 4). This is in contrast with what was described in previous allelic exchange attempts with other genes, where the vast majority of the analyzed clones, up to 80%, resulted from illegitimate rather than homologous recombination (1, 8). The differences could possibly be due to the length and the structure of the genes that have been employed.

Two-step Positive Selection of Allelic Exchange Mutants.

Figure 5:
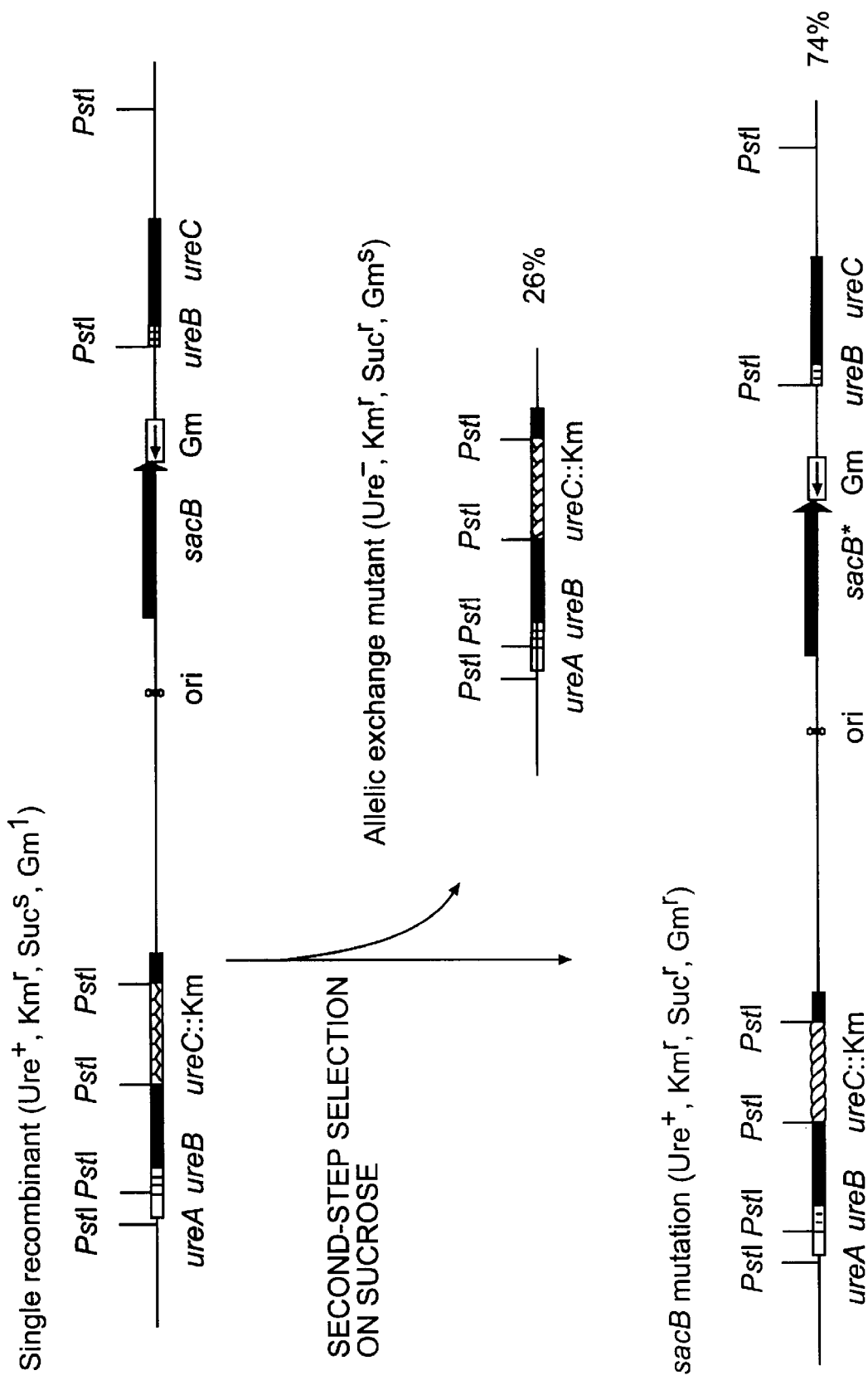
Figure 6:
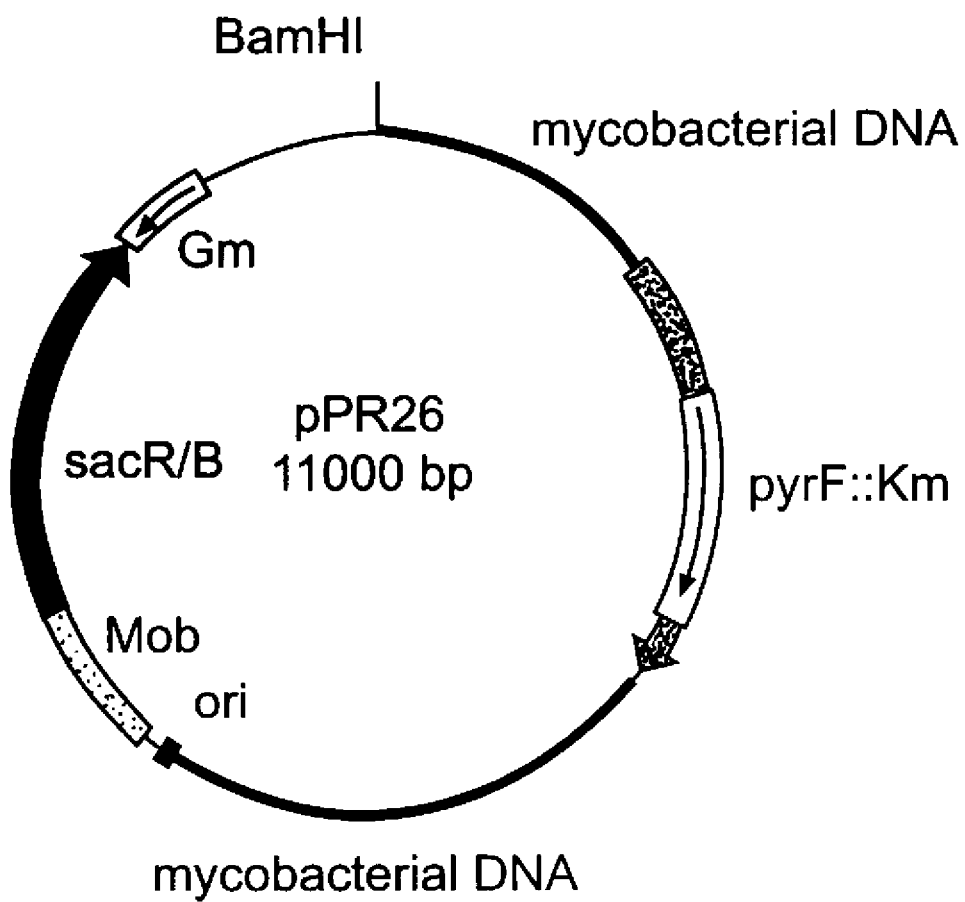
Figure 7:
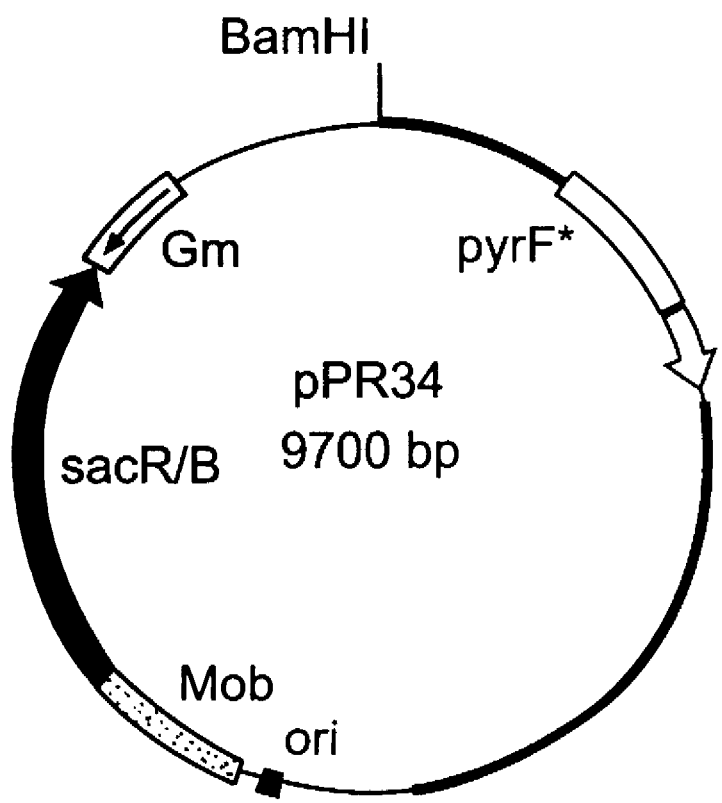
Figure 8:
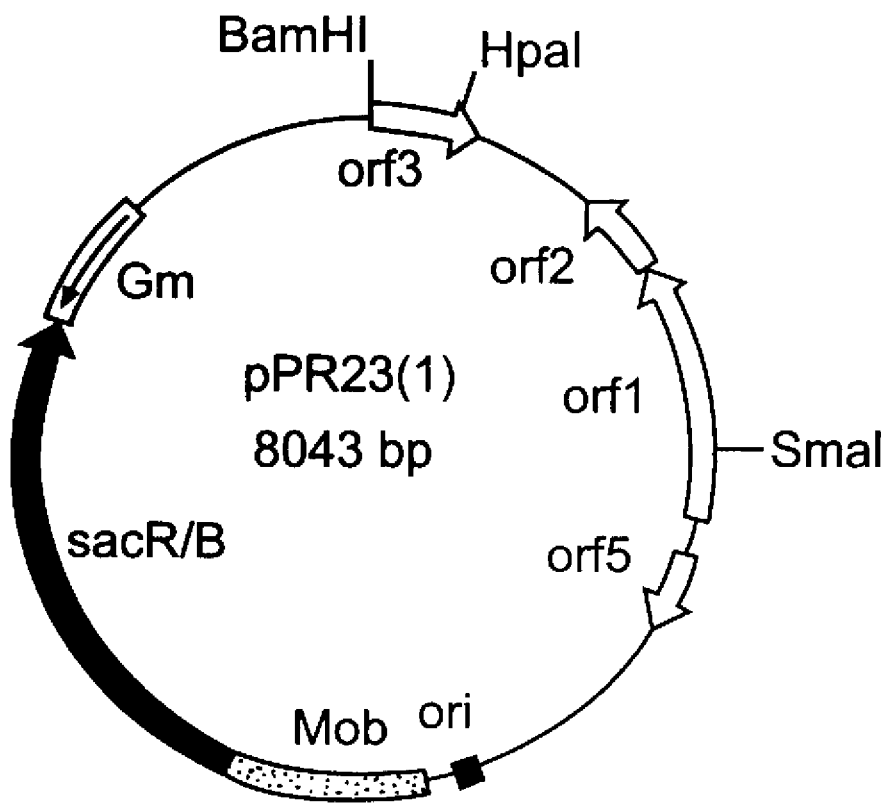
Figure 9:
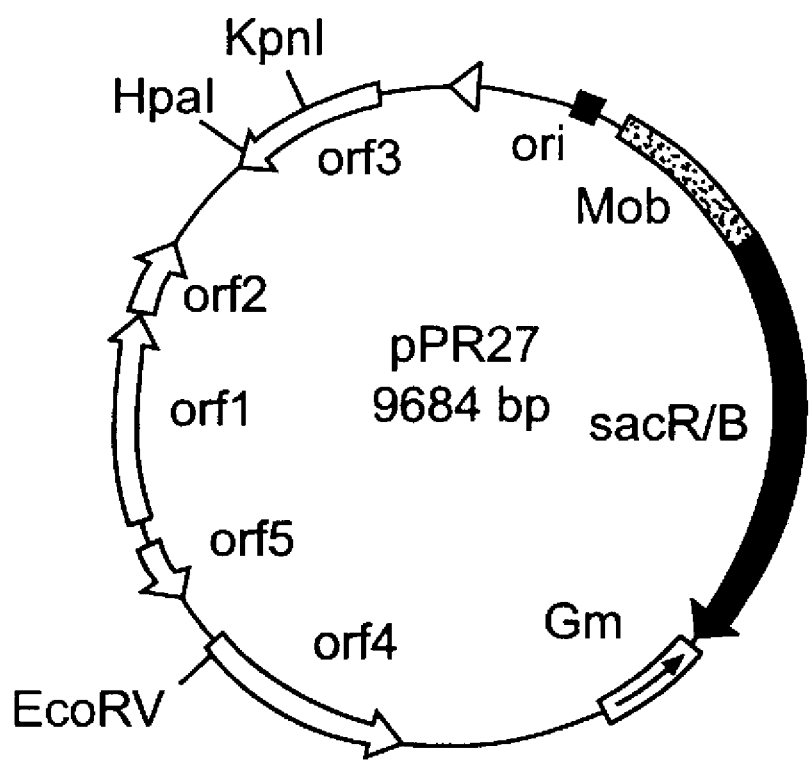
Figure 10:
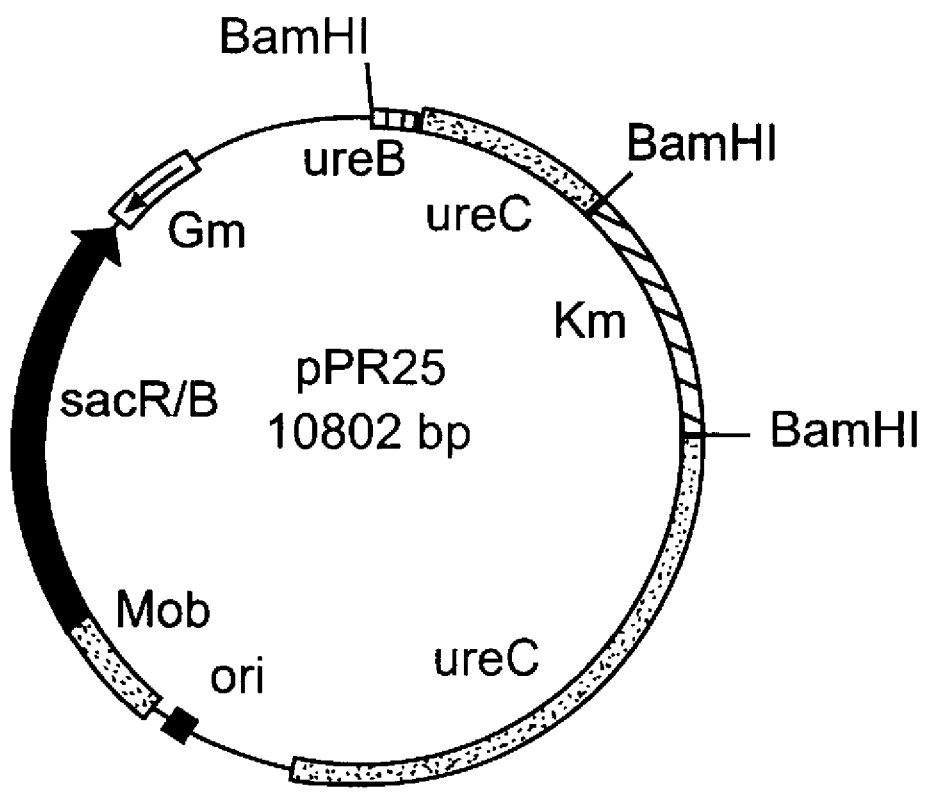
Figure 11:
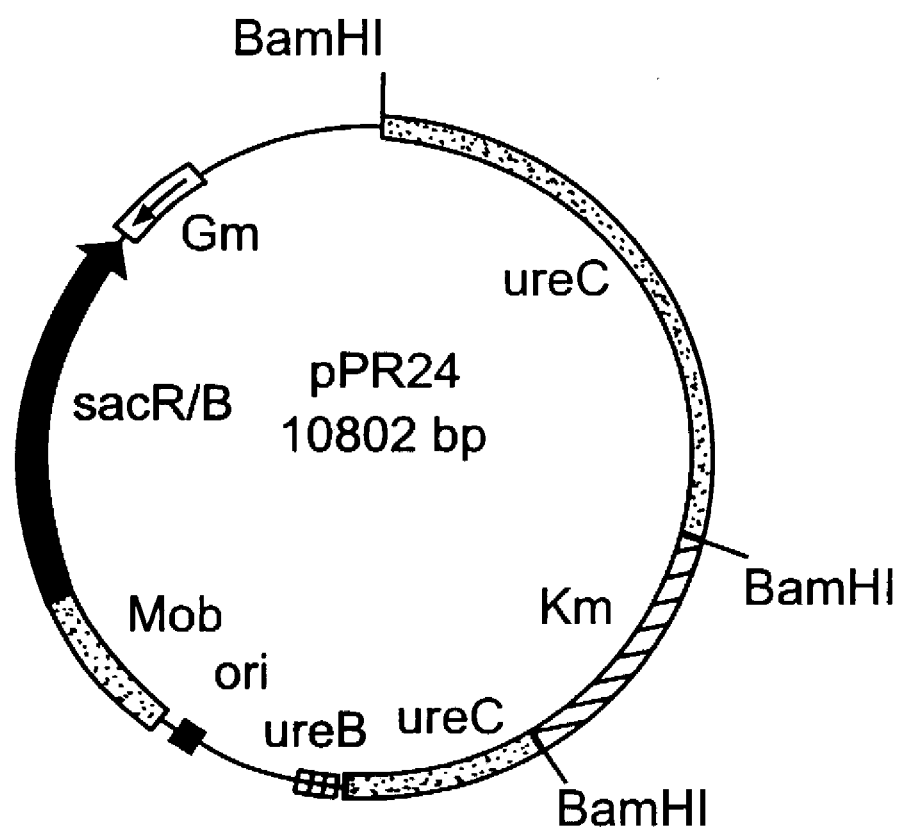
Figure 12:
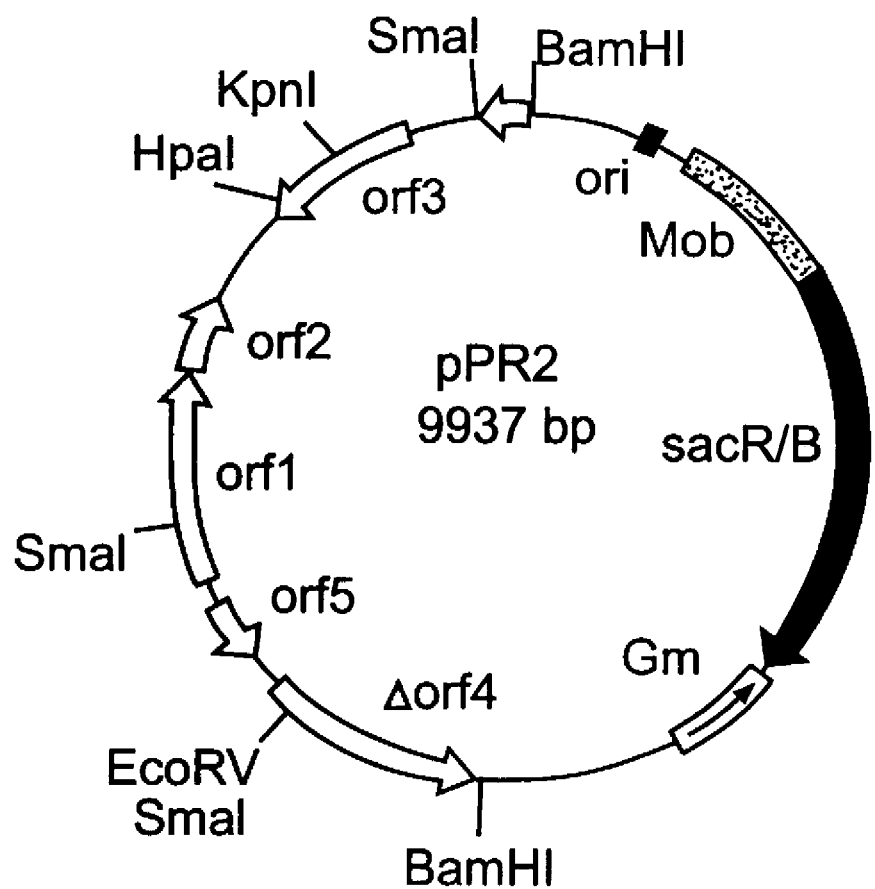

When propagated in 7H9 without antibiotic, the above described single-recombinants could undergo two changes that would render them Km$^r$, Suc$^r$. (i) Cells may lose the SacB gene during a second cross-over, (ii) SacB may be inactivated by a point mutation, a deletion or an insertion (FIG. 5). The frequency of the second homologous recombination event is very low, and was estimated at 10$^{-5}$ in *M. smegmatis* for the pyrF gene (4). Thus the detection of an allelic exchange mutant, though possible for a gene with a defined and an easily screenable phenotype is virtually impossible for the vast majority of genes where the screening is based on a Southern-blot experiment.

Cultures of the single recombinant clones were spread, at a 1/50 dilution, on 7H10-Km supplemented with 2% sucrose. In contrast to our previous experiments (13, 14), the concentration of sucrose was lowered to 2% because the growth of untransformed *M. bovis* BCG is dramatically slowed down in the presence of 10% sucrose (13). The efficiency of selection remained the same, whereas the growth rate was unaffected on 2% sucrose (13). 500 Suc$^r$, Km$^r$ colonies were obtained from one ml of culture, and 50 clones were analyzed by the phenotypic test. The proportion of Ure$^-$ mutants was much higher than in a classical experiment presenting a 6-fold increase (Table 4). Approximately one in four colonies tested (26%) corresponded to an allelic exchange mutant as also verified on a Southern-blot (FIG. 4). The remaining clones (74%) though Suc$^r$, were Ure$^-$ and presumably corresponded to clones with a mutation in the SacB gene. Their genomic DNA was probed with pPR24 in a Southern-blot experiment and this showed no apparent change of the vector size, suggesting that the SacB mutations were point mutations or micro-deletions (FIG. 4).

Unlike what was observed in *M. smegmatis*, with the pyrF gene, no mutants corresponding to the insertion of an IS element were observed (14).

In summary, it has been demonstrated that a two-step positive selection of allelic exchange mutants, using SacB as a counter-selectable marker, is possible and very efficient in the slow-growing *M. bovis* BCG. As for the results obtained in *M. smegmatis* using the same protocol (14), a high proportion of the clones selected on sucrose were allelic exchange mutants. In cases where the allelic exchange is possible using a classical protocol of mutagenesis, one-step selection on sucrose would greatly reduce the number of clones that have to be tested in order to isolate a mutant. In conclusion, a general protocol has been designed that should render the creation of defined mutants in bacteria of the *M. tuberculosis* complex much easier than it was until now, paving the way for further genetic characterization of this important pathogen. Moreover, this protocol should also make possible the creation of unmarked mutants, when the antibiotic resistance cassette in the gene is replaced by a frameshift mutation and the second-step selection is performed on sucrose medium without antibiotic pressure (14). It was already demonstrated for *M. smegmatis* (14) and other bacteria where the SacB gene can be used as a counter-selectable marker (3, 19).

Plasmids pPR23, pPR24, pPR25, pPR26, pPR27, pPR34, and pPR2 deposited under the provisions of the Budapest Treaty at the National Collection of Cultures of Microorganisms (C.N.C.M.) in Paris on Jun. 19, 1996, and assigned the following reference numbers:

pPR23—C.N.C.M. No. I-1726
pPR24—C.N.C.M. No. I-1727
pPR25—C.N.C.M. No. I-1728
pPR26—C.N.C.M. No. I-1729
pPR27—C.N.C.M. No. I-1730
pPR34—C.N.C.M. No. I-1731
pPR2—C.N.C.M. No. I-1725.

REFERENCES

Aldovini, A., Husson, R. N., and Young, R. A. (1993) The uraA locus and homologous recombination in *Mycobacterium bovis* BCG. *J. Bacteriol* 175:7282–7289.

Balasubramanian, V., Pavelka, Jr. M. S., Bardarov, S. S., Martin, J. Weisbrod, T. R., McAdam, R., Bloom. B. R., and Jacobs, Jr. W. R. (1996) Allelic exchange in *Mycobacterium tuberculosis* with long linear recombination substrates. *J. Bacteriol* 178:273–279.

Cai, Y., and Wolk, P. C. (1990) Use of a conditionally lethal gene in Anabaena sp. strain PCC7120 to select for double recombinants and to entrap insertion sequences. *J. Bacteriol* 172:3138–3145.

Clanciotto, N. P., Long, R., Eisenstein, B. I., and Engleberg, N. C. (1988) Site-specific mutagenesis in *Legionella pneumophila* by allelic exchange using counter-selectable ColE1 vectors. *FEMS Microbiol Lett* 56:203–208.

Cirillo, J. D.. Barletta, R. G., Bloom, B. R., and Jacobs, Jr, W. R. (1991) A novel transposon trap for mycobacteria: isolation and characterization of IS1096. *J. Bacteriol* 173:7772–7780.

Desomer, J., Crespi. M., and Van Montagu. M. (1991) Illegitimate integration of non-replicative vectors in the genome of *Rhodococcus fascians* upon electro-transformation as an insertional mutagenesis system. *Mol Microbiol* 5:2115–2124.

Donnenberg, M. S., and Kaper, J. B. (1991) Construction of an ese deletion mutant of enleropathogenic *Escherichia* coli by using a positive-selection suicide vector. *Infect Immun* 59:4310–4317.

Falkow, S. (1988) Molecular Koch's postulates applied to microbial pathogenicity. *Rev Infec Dis* 10:S274–S276.

Gay, P., Le Coq, D., Steinmetz, M. Berkelman, To., and Kado C. I. (1985) Positive selection procedure for entrapment of insertion sequence elements in Gram-negative bacteria. *J. Bacteriol* 164:918–921.

Husson, R. N., James, B. E., and Young, R. A. (1990) Gene and expression of foreign DNA in mycobacteria. *J. Bacteriol* 172:519–524.

Jacobs, Jr., W. R. (1992) Advances in mycobacterial genetics: new promises for old diseases. *Immunobiology* 184:147–156.

Jacobs, Jr., W. R., Kalpana, G. V., Cirillo, J. D., Pascopella, L., Snapper, S. B., Udani, R. A., Jones, W. Barletta, R. G., and Bloom, B. R. (1991) Genetic systems for mycobacteria, *Meth Enzymol* 204:537–555.

Kalpana, G. V., Bloom, B. R., and Jacobs, Jr. W. R. (1991), Insertional mutagenesis and illegitimate recombination in mycobacteria. *Proc Natl Acad Sci USA* 88:5433–5437.

Kamoun, S., Tola, E., Kamdar, H., and Kado, C. I. (1992). Rapid generation of directed and unmarked deletions in *Xanthomonas*. *Mol Microbiol* 6:809–816.

Kaniga, K., Delor, I., and Cornells, G. R. (1991) A wide-host-range suicide vector for improving reverse genetics in Gram-negative bacteria: Inactivation of the blaA gene of *Yersinla enterocolitca*. *Gene* 109:137–141.

Marklund, B. I., Speert, D. P., and Stokes, R. W. (1995) Gene replacement through homologous recombination in *Mycobacterium intracellulare. J. Bacteriol* 177:6100–6105.

Norman, E., Dellagostin, O. A., McFadden, J., and Dale, J. W. (1995) Gene replacement by homologous recombination in *Mycobacterium bovis* BCG. *Mol Microbiol* 16:755–760.

Pelicic, V., Reyrat, J. M., and Gicquet, B. (1996) Expression of the *Bacillus subtillis* SacB gene confers sucrose sensitivity on mycobacteria. *J. Bacteriol* 178:1197–1199.

Quandt, J., and Hynes, M. F. (1993) Versatile suicide vectors which allow direct selection for gene replacement in Gramm-negative bacteria. *Gene* 127:15–21.

Reyrat, J. M., Berthet, F. -X, and Gloquel, B. (1995) The urease locus of *Mycobacterium tuberculosis* and its utilization for the demonstration of allelic exchange in *Mycobacterium bovis* bacillus Camette-Guèrlin. *Proc Natl Acad Sci USA* 92:8768–8772.

Ried, J. L., and Collmer, A. (1987) An nptl-sacb-sacR cartridge for constructing directed, unmarked mutations in Gram-negative bacteria by marker exchange-eviction mutagenesis. *Gene* 57:239–246.

Ruvkin, G. B., and Ausubel, F. M. (1981) A general method for site-directed mutagenesis in prokaryotes. *Nature* 289:85–88.

Sambrook, J., Fritsch, E. F., and Manlatis, T. (1989) *Molecular Cloning: A Laboratory Manual.* 2nd edn. Cold Spring Harbor, N.Y.: Cold Spring Harbor Laboratory Press.

Sander, P., Meier, A., and Bottger, E. C. (1995) rpst+ a dominant selectable marker for gene replacement in mycobacteria. *Mol Microbiol* 16:991–1000.

Schafer, A., Tauch, a. Jager, W., Kalinowski, J., Thierbach, G., and Pohler, A. (1994) Small mobilizable multi-purpose cloning vectors derived from the *Eschericha coli* pK18 and pK19: selection of defined deletions in the chromosome of *Corynebacterium glutamicum*. *Gene* 45:69–73.

Schweizer, H. P. (1992) Allelic exchange in *Pseudomonas aeruginosa* using novel ColE1-type vectors and a family of cassettes containing a portable oriT and the counterselectable *Bacillus subtilis* SacB marker. *Mol Microbiol* 6:1195–1204.

Snapper, S. B., Melton, R. E. Mustapha, S. Keiser, To., and Jacobs, Jr., W. R. (1990) Isolation and characterization of efficient plasmid transformation mutants of *Mycobacterium smegmatis: Mol Microbiol* 4:1911–1919.

Soupène, E. Foussard, M. Bolstard, P., Truchet, G., and Batut, J. (1955) Oxygen as a key developmental regulator of *Rhizobium melilot* $N_2$-fixation gene expression within the alfalfa root nodule. *Proc Natl Acad Sci USA* 92:3759–3763.

Stibitz, S. (1994) Use of conditionally counter-selectable suicide vectors for allelic exchange. *Meth Enzymol* 235:458–465.

WHO (1991) Streptomycin. In *drugs used in mycobacterial infections.* Geneva: World Health Organization.

1. Aldovini, A., R. N. Husson, and R. A. Young. 1993. The ura locus and homologous recombination in *Mycobacterium bovis* BCG. *J. Bacteriol.* 175:7281–7289.

2. Balasubramanian, V., M. S. Pavelka Jr., S. S. Bardarov, J. Martin, T. R. Weisbrod, R. A. McAdam, B. R. Bloom, and W. R. Jacobs Jr. 1996. Allelic exchange in *Mycobacterium tuberculosis* with long linear recombination substrates. *J. Bacteriol.* 178:273–279.

3. Donnenberg, M. S., and J. B. Kaper. 1991. Construction of an eae deletion mutant of enteropathogenic *Escherichia coli* by using a positive-selection suicide vector. Infect. Immun. 59:4310–4317.

4. Husson, R. N., B. E. James, and R. A. Young. 1990. Gene replacement and expression of foreign DNA in mycobacteria. J. Bacteriol. 172:519–524.

5. Jacobs, W. R. 1992. Advances in mycobacterial genetics: new promises for old diseases. Immunobiol. 184:147–156.

6. Jacobs, W. R., G. V. Kalpana, J. D. Cirillo, L. Pascopella, S. B. Snapper, R. A. Udani, W. Jones, R. G. Barletta, and B. R. Bloom. 1991. Genetic systems for mycobacteria. Methods Enzymol. 204:537–555.

7. Jackson, M. Personal communication.

8. Kalpana, G. V., B. R. Bloom, and W. R. Jacobs, Jr. 1991. Insertional mutagenesis and illegitimate recombination in mycobacteria. Proc. Natl. Acad. Sci. USA. 88:5433–5437.

9. Kamoun, S., E. Tolla, H. Kamdar, and C. I. Kado. 1992. Rapid generation of directed unmarked deletions in *Xanthomonas. Mol. Microbiol.* 6:809–816.

10. Marklund, B. -I., D. P. Speert, and R. W. Stokes. 1995. Gene replacement through homologous recombination in *Mycobacterium intracellulare.* J. Bacteriol. 177:6100–6105.

11. Meyer, L., and H. L. David. 1979. Evaluation de l'activité uréase et de l'activité β=glucosidase pour l'identification pratique des mycobactéries. Ann. Inst. Pasteur Microbiol. 130B:323–332.

12. Norman, E., O. Q. Dellagostin, J. McFadden, and J. W. Dale. 1995. Gene replacement by homologous recombination in *Mycobacterium bovis* BCG. Mol. Microbiol. 16:755–760.

13. Pelicic, V., J. -M. Reyrat, and B. Gicquel. 1996. Expression of the *Bacillus subtilis* SacB gene confers sucrose sensitivity on mycobacteria. J. Bacteriol. 178:1197–1199.

14. Pelicic, V. J. -M Reyra, and B. Gicquel. 1996. Generation of unmarked directed mutations in mycobacteria, using sucrose counter-selectable suicide vectors. Mol. Microbiol. in press.

15. Quandt, J., and M. F. Hynes. 1993. Versatile suicide vectors which allow direct selection for gene replacement in Gram-negative bacteria. Gene. 127:15–21.

16. Reyrat, J. -M., F. -X. Berthet, and B. Gicquel. 1995. The urease locus of *Mycobacterium tuberculosis* and its utilization for the demonstration of allelic exchange in *Mycobacterium bovis* bacillus Calmette-Guérin. Proc. Natl. Acad. Sc. USA. 92:8768–8772.

17. Ruvkun, G. B., and F. M. Ausubel. 1981. A general method for site-directed mutagenesis in prokaryotes. Nature. 289:85–88.

18. Sander, P., A. Meier, and E. C. Böttger. 1995. rpsL$^+$: a dominant selectable marker for gene replacement in mycobacteria. Mol. Microbiol. 16:991–1000.

19. Schweizer, H. P. 1992. Allelic exchange in *Pseudomonas aeruginosa* using novel ColE1-type vectors and a family of cassettes containing a portable oriT and the counter-selectable *Bacillus subtilis* SacB marker. Mol. Microbiol. 6:1195–1204.

20. Stibitz, S. 1994. Use of conditionally counter-selectable suicide vectors for allelic exchange. Methods Enzymol. 235:458–465.

What is claimed is:

1. A process for replacing a nucleotide sequence in the genome of a mycobacterium, strain comprising the steps of:
   a) providing a vector containing SacB gene coding for levansucrase enzyme and a nucleotide sequence of interest;
   b) transforming the mycobacterium strain with said vector;
   c) selecting clones of the resulting transformed mycobacteria in which a nucleotide sequence in the genome has been replaced by the nucleotide sequence of interest by propagating said transformed clones in a culture medium supplemented with sucrose; and
   d) isolating a strain in which a nucleotide sequence in the genome has been replaced.

2. The process according to claim 1, wherein the vector contains a marker gene, and wherein step c) is preceded by a first selection step of the clones by propagating said clones in a culture medium supplemented with a selection molecule.

3. The process according to claim 2, wherein the marker gene is a gene coding for resistance to an antibiotic.

4. The process according to claim 3, wherein the antibiotic resistance coding gene is the gene coding for gentamycin resistance.

5. The process according to anyone of claim 1 to 4, wherein the nucleotide sequence of interest is an endogenous gene of the mycobacteria to be transformed that has been modified by addition, substitution, or deletion of at least one nucleotide.

6. The process according to anyone of claims 1 to 4, wherein the nucleotide sequence of interest is a hybrid DNA molecule containing an exogenous nucleotide sequence with respect to the mycobacteria to be transformed, which exogenous nucleotide sequence is bordered at its 5' and 3' ends by a nucleotide sequence that is endogenous with respect to the mycobacteria to be transformed.

7. The process according to anyone of claims 1 to 4, wherein the nucleotide sequence of interest is a hybrid molecule coding for a fusion polypeptide.

8. The process according to anyone of claims 1 to 4, wherein the mycobacterium strain is *M. tuberculosis*.

9. The process according to anyone of claim 1 to 4 wherein the mycobacterium strain is *M. smegmatis*.

10. The process according to claim 1, wherein the nucleotide sequence to be replaced is a plasmidic or a chromosomal nucleotide sequence.

11. The process according to claim 7, wherein the fusion polypeptide contains an antigenic determinant heterologous with respect to the mycobacterium strain to be transformed.

12. Recombinant vector pPR24 (C.N.C.M. No. I-1727).
13. Recombinant vector pPR25 (C.N.C.M. No. I-1728).
14. Recombinant vector pPR2 (C.N.C.M. No. I-1725).
15. Recombinant vector pPR26 (C.N.C.M. No. I-1729).
16. Recombinant vector pPR34 (C.N.C.M. No. I-1731).

17. A method for selecting mycobacteria transformed with the SacB gene comprising the steps of:
   a) providing a vector containing SacB gene coding for levansucrase enzyme;
   b) transforming a mycobacterium strain with said vector;
   c) cultivating the resulting transformed mycobacteria in a culture medium supplemented with sucrose;
   d) cultivating in parallel the same transformed mycobacteria in a culture medium without sucrose; and
   e) selecting clones sensitive to sucrose, indicating mycobacteria which have been transformed with the SacB gene.

18. A process for inserting a nucleotide sequence of interest in the genome of a slow growing mycobacterium strain comprising the steps of:
   a) providing a vector containing SacB gene coding for levansucrase enzyme and said nucleotide sequence of interest;
   b) transforming the slow growing bacterium with the vector of step a);
   c) selecting clones of the resulting transformed mycobacteria in which said nucleotide sequence of interest has been inserted by propagating said clones in a culture medium supplemented with sucrose; and
   d) isolating a strain in which said nucleotide sequence of interest has been inserted.

19. The process according to claim 18, wherein the vector contains a marker gene, and wherein step c) is preceded by a first selection step of the recombinant clones by propagating said clones in a culture medium supplemented with a selection molecule.

20. The process according to claim 19, wherein the marker gene is a gene coding for an antibiotic resistance.

21. The process according to claim 19, wherein the antibiotic resistance gene is the gene coding for resistance to gentamycin.

22. The process according to anyone of claims 18 to 21, wherein the nucleotide sequence of interest is an insertion sequence.

23. The process according to claim 22, wherein the insertion sequence is a transposon.

24. The process according to claim 23, wherein the transposon is Tn611.

25. Recombinant vector pPR23 (C.N.C.M. No. I-1726).
26. Recombinant vector pPR27 (C.N.C.M. No. I-1730).

* * * * *